United States Patent
Min et al.

(10) Patent No.: US 7,706,872 B2
(45) Date of Patent: Apr. 27, 2010

(54) METHOD AND DEVICE FOR MEASUREMENT OF ELECTRICAL BIOIMPEDANCE

(75) Inventors: Mart Min, Tallinn (EE); Andres Kink, Kiili (EE); Raul Land, Tallinn (EE); Toomas Parve, Tallinn (EE)

(73) Assignee: Tallinn Technical University, Tallinn (EE)

( * ) Notice: Subject to any disclaimer, the term of this patent is extended or adjusted under 35 U.S.C. 154(b) by 927 days.

(21) Appl. No.: 10/537,643

(22) PCT Filed: Nov. 28, 2003

(86) PCT No.: PCT/EE03/00006

§ 371 (c)(1),
(2), (4) Date: Jun. 6, 2005

(87) PCT Pub. No.: WO2004/052198

PCT Pub. Date: Jun. 24, 2004

(65) Prior Publication Data

US 2006/0100539 A1  May 11, 2006

(30) Foreign Application Priority Data

Dec. 6, 2002 (EE) .................................. 200200677

(51) Int. Cl.
*A61B 5/05* (2006.01)
(52) U.S. Cl. ....................... 600/547; 324/525
(58) Field of Classification Search ................ 600/547, 600/536; 378/70; 607/88; 324/525

See application file for complete search history.

(56) References Cited

U.S. PATENT DOCUMENTS 5,063,937 A * 11/1991 Ezenwa et al. .............. 600/536

(Continued)

FOREIGN PATENT DOCUMENTS

WO    WO 00/57953    10/2000

(Continued)

OTHER PUBLICATIONS

A. Eek et al., "Electrical Bio-Impedance Measurement in a Rate-adaptive Pacemaker", 1996, 4p.*

(Continued)

*Primary Examiner*—Max Hindenburg
*Assistant Examiner*—Renee Danega
(74) *Attorney, Agent, or Firm*—Vern Maine & Associates

(57) ABSTRACT

A method of measuring of an electrical bio-impedance, the method being characterized in that a symmetrical bipolar pulse-form periodical excitation signal (electrical current or voltage) is applied to the input (11) of the bio-object (1), a corresponding reaction of the bio-object to the mentioned excitation signal is measured from the output (12), which is connected to the input (201) of the synchronous detector (200). A symmetrical bipolar pulse-form periodical signal is also applied to the reference input (202) of the synchronous detector (200), whereby both pulse-form signals are shortened by the predetermined time interval in each half period of the signal, said time intervals being different for the excitation and reference signals. The proposed method ensures an increased accuracy of the impedance analysis by decreasing the influence of the higher harmonics in the spectra of the excitation and reference signals of the synchronous detectors to the measurement result. The use of the rectangular signals ensures that the device for implementing of the proposed method has a simple design and low power consumption.

6 Claims, 6 Drawing Sheets

U.S. PATENT DOCUMENTS

| | | | |
|---|---|---|---|
| 5,759,159 | A | 6/1998 | Masreliez |
| 6,320,370 | B1 * | 11/2001 | Weggel .................. 324/117 R |
| 6,377,845 | B1 * | 4/2002 | Kinast ........................ 600/547 |
| 6,473,640 | B1 | 10/2002 | Erlebacher |
| 6,885,892 | B1 | 4/2005 | Min et al. |
| 6,975,903 | B1 | 12/2005 | Min et al. |

FOREIGN PATENT DOCUMENTS

| | | |
|---|---|---|
| WO | WO 00/57954 | 10/2000 |
| WO | WO 01/19426 A2 | 3/2001 |

OTHER PUBLICATIONS

Mart Min et al., "An Implantable Analyzer of Bio-Impedance Dynamics: Mixed Signal Approach", 2000, IEEE, 5p.*

Min et al. "Design Concepts of Instruments for Vector Parameter Identification" IEEE Transactions on Instrumentation and Measurement vol. 4, Feb. 1992, pp. 1-4.*

Pradeep et al. "Generalized Structure of a Multilevel PWM Inverter" IEEE transactions on industry applications Nov./Dec. 1983. pp. 1-5).*

Min, Mart, et al., "Lock-in measurement of bio-impedance variations", Measurement, 2000, pp. 21-28, vol. 27, Elsevier Science Ltd.

Min, Mart, et al., "Improvement of the vector analyser based on two-phase switching mode synchronous detection", Measurement, 1997, pp. 103-111, vol. 19, No. 2, Elsevier Science Ltd.

Goovaerts, H.G., et. al., "A wideband high common mode rejection ratio amplifier and phase-locked loop demodulator for multifrequency impedance measurement", Medical & Biological Engineering & Computing, Nov. 1998, pp. 761-767, vol. XP-000784850.

Min, Mart, et al., "Design Concepts of Instruments for Vector Parameter Identification", IEEE Transactions on Instrumentation and Measurement, Feb. 1992, pp. 50-53, vol. 41, No. 1.

* cited by examiner

METHOD AND DEVICE FOR MEASUREMENT OF ELECTRICAL BIOIMPEDANCE

RELATED APPLICATIONS

This application is a national phase application of PCT Application Serial NumberPCT/EE2003/000006 filed Nov. 28, 2003, which, in turn, claims priority to Estonian Application No. P200200677, filed Dec. 6, 2002. Each of these applications is herein incorporated in its entirety by reference.

TECHNICAL FIELD

The invention is related to the measurement of electrical impedance, particularly to measurement of the electrical bio-impedance, and is based on the synchronous signal conversion or lock-in techniques used for converting of measuring signals for forming the measuring (excitation) signal as well as for demodulating the response signal from the object.

The main field of application of the invention is related to the measurement of impedance in portable and/or implantable medical means and apparatuses, which are used with the aim to get diagnostic results and to determine the conditions of implanted and/or implantable and transplantable organs and tissues. The invention is directly aimed to be used in implantable medical devices, such as rate-adaptive cardiac pacemakers and monitors, and in monitors of transplantable and transplanted organs.

BACKGROUND

The PCT application WO 01/19426 "Implantable Device and Method for Long-Term Detection and Monitoring of Congestive Heart Failure" has been described a measuring device, which is mounted into the pacemaker, and observes over the complications appearing in the cardiac blood vessel system and in the blood circulation in lungs. The method is based on directing various types of current/voltage excitation signals (rectangular waveform signal, sine wave signal, pulse signal, signal with varying frequency) through the bio-object and measuring the inphase and quadrature components of the electrical response to the excitation. The device measures the variations in the impedance of the cardiac blood vessel system and of the blood circulation in lungs via measuring the current flow through the object, the voltage drop forming on it and the phase shift between the excitation and response signals.

In the inventions WO 00/57953 and WO 00/57954 "A Rate Adaptive pacemaker" the device for bio-impedance measurement is used for obtaining information for adaptive control of cardiac pacing rate taking into account the energetic balance of the myocardium.

U.S. Pat. No. 5,759,159 "Method and Apparatus for Apical Detection with Complex Impedance Measurement" (Jun. 2, 1998) describes the bio-impedance measurement device used for finding the apex of a dental channel. The apex can be found by measuring the amplitude and phase characteristics of the bio-impedance between the probe and biological tissue. The method is based on measuring the amplitude and phase relationships of an electrical impedance in response to a multi-frequency excitation using a digital fast Fourier transformation (FFT).

The above described devices are not suitable for implantation because their electronic circuitry is too complicated and energy consuming.

Nowadays low voltage and low power CMOS microelectronics technology is suitable for application in switching mode analogue and digital mixed signal circuits. The extremely low power consumption is crucially important for the implantable devices operating during several years with the same battery.

Unfortunately, application of the switching mode electronics operating with pulse signals results in misleading measurement errors and measurement uncertainties due to the higher harmonics present in the pulse signals. Theoretically, application of pure sine wave signals without any higher harmonics is presumed for determination of the complex impedance. Therefore, application of the simplest rectangular waveform pulses being the most suitable for use in CMOS electronics, introduces serious measurement errors [M. Min, and T. Parve, "*Improvement of the vector analyser based on two-phase switching mode synchronous detection*", *Measurement*, Vol. 19 (1996), No. 2, pp. 103-111].

To overcome the problem, usually the band-pass filters are introduced in order to filter out the fundamental and to suppress the higher harmonics. This solution helps to solve the higher harmonics problem only partly, because the highly selective band-pass filters have very unstable phase characteristics. The exact tuning of such filters is also rather complicated.

U.S. Pat. No. 5,063,937, A61B 5/05, "Multiple frequency bio-impedance measurement system", B. N. Ezenwa, W. P. Couch, Nov. 12, 1991, describes the closest reference. In this document there is described a solution for a device for non-invasive measurement of the bio-impedance of a living tissue, according to which the component of interest of the excitation response of the bio-impedance (its active or reactive part) is demodulated by a synchronous detector, the reference signal of which is a rectangular wave signal being in phase or in quadrature with the excitation signal.

The systems operation is based on the switch-mode generator generating rectangular pulses, but prior to being applied to the test objects input the excitation pulses pass the highly selective band-pass filter. The band-pass filter is tuned to the main frequency of the excitation signal, and therefore the filter suppresses the higher harmonics of the original rectangular pulses, reducing in such a way the content of higher harmonics in the signals to be detected by the synchronous detector and decreasing measurement errors, which are caused by higher harmonics.

The described above solution has the following main drawbacks.

Tuning of a highly selective band-bass filter to the fundamental frequency is a troublesome procedure with an instable result. The phase shift between input and output can be compensated using sophisticated electronic circuits, which makes the excitation generator excessively complicated and bulky.

Some problems arise also in connection with generating of the reference signals used for driving the synchronous detector. In practice the rectangular reference pulse signals have to be formed anew from the filtered out pure sine wave excitation signal in order to eliminate the phase errors caused by the highly selective filter. Thus, some additional electronic circuits are needed, but the complexity of a circuitry is extremely undesirable in implantable medical devices in connection with which the compactness and low current consumption is required.

In addition, the described solution is not suitable for implementing in modern CMOS technology because several electronic blocks operate in near to linear mode.

SUMMARY OF THE INVENTION

The purpose of the invention is to increase the accuracy of measurements of the electrical impedance and/or immittance, using the switch-mode generation and demodulation of signals in the case of both analogue and digital signal processing, retaining at the same time the characteristic simplicity of the measurement method, as well as the simplicity and low energy consumption of the measuring device. The undesirable effects caused by both the higher odd harmonics contained in the rectangular wave signals and by the sensitivity of traditional synchronous detectors to odd higher harmonics are essentially suppressed, minimized, or in some embodiments, eliminated.

In traditional applications of synchronous detectors the strongest impact to the demodulated signal is caused by the closest to the main frequency odd higher harmonics within the first decade, i.e. the 3rd, 5th, 7th, and 9th harmonics, having typically the highest levels as well. For example, the measurement error caused only by the 3rd harmonic of the rectangular signal having the level of ⅓ of the fundamental, can cause a relative measurement error of ⅑ or 11 percent. The resulting measurement error from all higher harmonics of the rectangular waveform can extend up to 24 percent.

In addition to the amplitude errors also the phase errors appear from application of the non sine wave signals. Though the phase errors remain relatively smaller than the amplitude errors, their role can be significant anyway, because the absolute value of the phase shift as a rule does not exceed 45 degrees at the bio-impedance measurements. Therefore, the phase error of only some degrees results in a relative error in the range of 10 percent.

A feature of one measurement method according to the invention lies in reducing of the harmonics content of periodic and symmetrically bipolar pulse wave signals through shortening the duration of their constant value sections by a predetermined time intervals, during which the signals can have different values, including the zero value (FIG. 2A). The zero value signal intervals present the simplest case of the method. The zero value means an absence of the signals physically and denote a stepwise transition of the signal from one discrete value to another. These signal transitions can be, but must not be stepwise in principle. For example, the transitions can have different stepwise forms, or completely or piecewise linear forms as well. Only the shortening of the constant value sections of the signals by the predetermined time intervals has the principal significance.

The zero value intervals in FIG. 2A are determined so that the spectrum of the excitation signal will not contain the 3rd harmonic and the spectrum of the reference signal driving the synchronous detector will not contain the 5th harmonic. In the respective mathematical expression for the spectrum of the shortened rectangular wave signal $$f(x) = \frac{4a}{\pi}\left[\frac{\cos b}{1}\sin x + \frac{\cos 3b}{3}\sin 3x + \frac{\cos 5b}{5}\sin 5x + \ldots\right] =$$

$$\frac{4a}{\pi}\sum_{n=0}^{\infty}\frac{\cos(2n+1)b}{2n+1} \times \sin(2n+1)x,$$

where:

a is the constant amplitude value of the pulse signal, and b characterises the relative shortening of pulses and is equal to the length of the signal's zero value interval within one half period, and can have values in the range of $b=0 \ldots \pi/2$ all these terms of the sum, for which the argument $(2n+1)b$ of the cosine function is an odd number multiple of $\pi/2$, that is $$(2n+1)b = \frac{\pi}{2} \times (2n+1)$$

are missing.

Whereas the lower order higher harmonics cause the most significant errors of synchronous demodulation, then the values for the zero value intervals b can be found from the following simple conditions:

to remove the 3rd harmonic, $3b=\pi/2, \Rightarrow b=\pi/6$ or 30°, to remove the 5th harmonic, $5b=\pi/2, \Rightarrow b=\pi/10$ or 18°.

Applying of the above given conditions shows that the first coinciding harmonics in the excitation and reference signals are the 7th ones, which means that the measurement error is reduced about one order in comparison with the initial case of using regular rectangular waveforms (the amplitude error between −13 to +24 percent is reduced to −1.8 to +2.4 percent). Such a result meets the needs of most cases to be faced in practice.

A device for implementing of the above method for increasing the accuracy of bio-impedance measurements contains additional functional blocks, the task of which is to shorten the duration of the constant value sections of both the excitation and the reference pulse signals by predetermined time intervals proportional to the signals periods, whereby these predetermined time intervals for the excitation signal and the reference signal have different duration.

DESCRIPTION OF THE INVENTION

Figure 1:
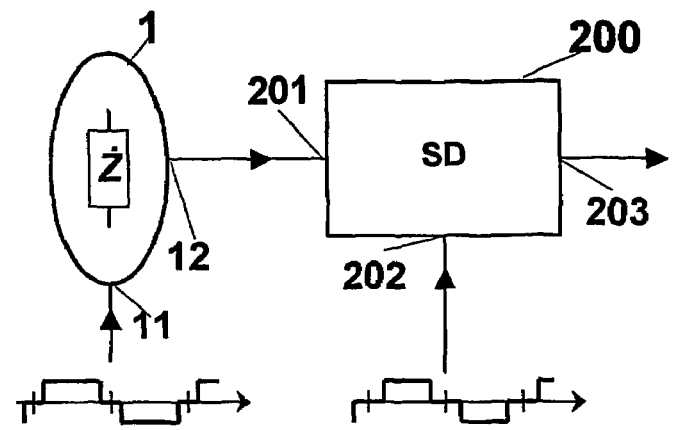
FIG. 1 is a simplified graphical presentation of the method for measurement of the electrical bio-impedance together with the signal waveforms of inputs.

FIG. 1 presents the method for measurement of the electrical impedance of bio-object is described. A symmetrical bipolar pulse-form periodical excitation signal (electrical current or voltage) is applied to the input 11 of the bio-object 1, a corresponding reaction of the bio-object to the mentioned excitation signal is measured from the output 12, which is connected to the input 201 of the synchronous detector 200. A symmetrical bipolar pulse-form periodical signal is also applied to the reference input 202 of the synchronous detector 200, but it has different spectral content in comparison with the excitation signal applied to the input 11 of the bio-object 1.

Figure 2A:
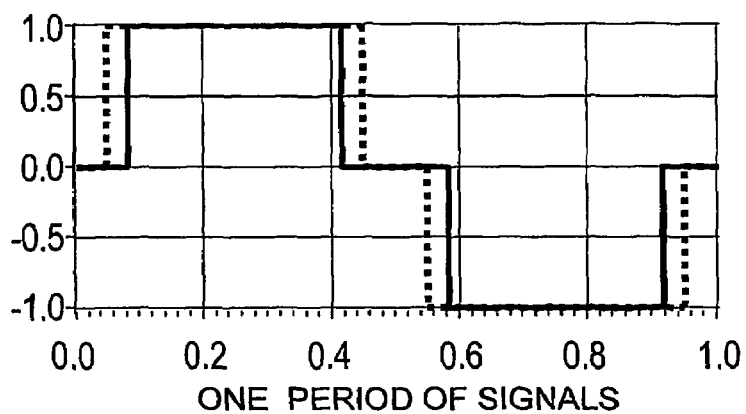
FIG. 2A shows on period of differently shortened rectangular wave pulse signals.
Figure 7:
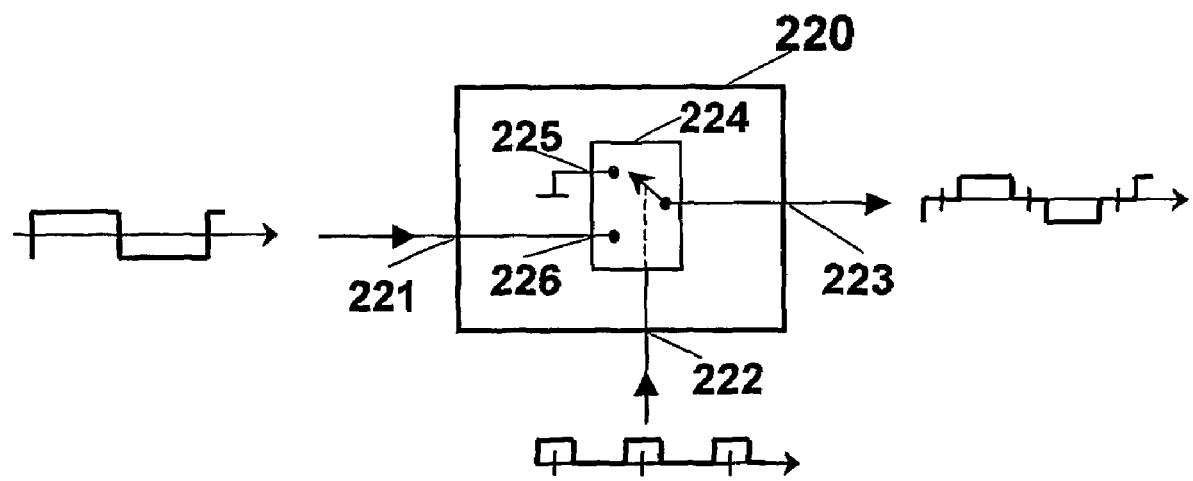
FIG. 7 is a generator of shortened pulses, whereby the signal waveforms are shown at the inputs and outputs.

Multiplication of pulse-form signals causes misleading measurement errors and uncertainty of results because of their higher harmonics content. Therefore, a former of shortened pulse 220 (FIG. 7) is used in the proposed solution, the task of which is to shorten the bipolar rectangular signal so that by introducing the zero value intervals certain spectral components of the signal are removed. For minimization of measuring error the zero value intervals introduced into the excitation and reference signals must be set different (FIG. 2A) so that the cut-offs of spectral components in these signals are placed in different locations on the axis of harmonics, thus providing a minimum number of error causing coinciding spectral components.

Figure 2B:
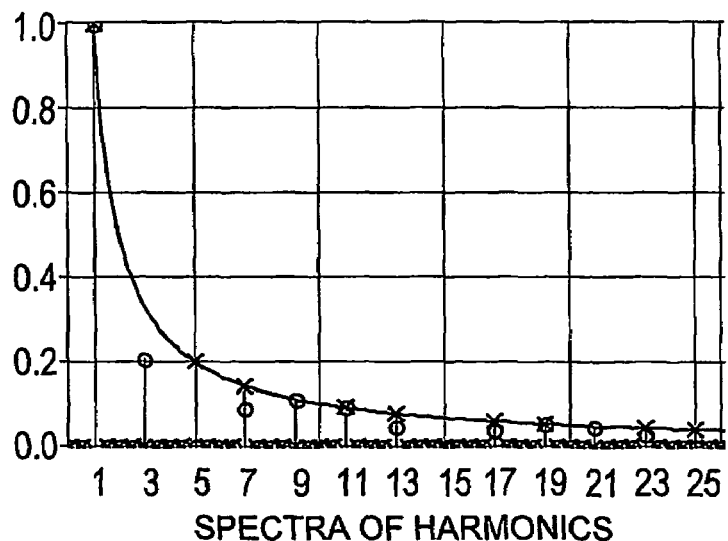
FIG. 2B gives the spectra of harmonics of the two shortened signals shown in FIG. 2A, where the harmonics designated with "x" correspond to the shorter pulse signal and with "o" to the wider one.

For example, if the zero value interval introduced into the excitation signal has a duration equal to $b=\pi/10$ or $18°$, then the excitation signal does not contain harmonics of the 5th, 15th, 25th, ... order, and if the zero value interval introduced into the reference signal is $b=\pi/6$ or $30°$, then the reference signal do not contain harmonics of the 3rd, 9th, 15th, ... order, and accordingly in the spectra of these signals the first coinciding harmonics having non-zero value are the $7^{th}$ harmonics (FIG. 2B), which determine the greatest portion of the residual measurement error.

In comparison with the known solutions based on using of rectangular signals the proposed method has an error level, which is approximately one decimal order smaller at the output 203 of the synchronous detector 200 (maximum measurement error is reduced from 24% to 2.5%), which is an error level acceptable for most practical measurements in the respective field.

Figure 3:
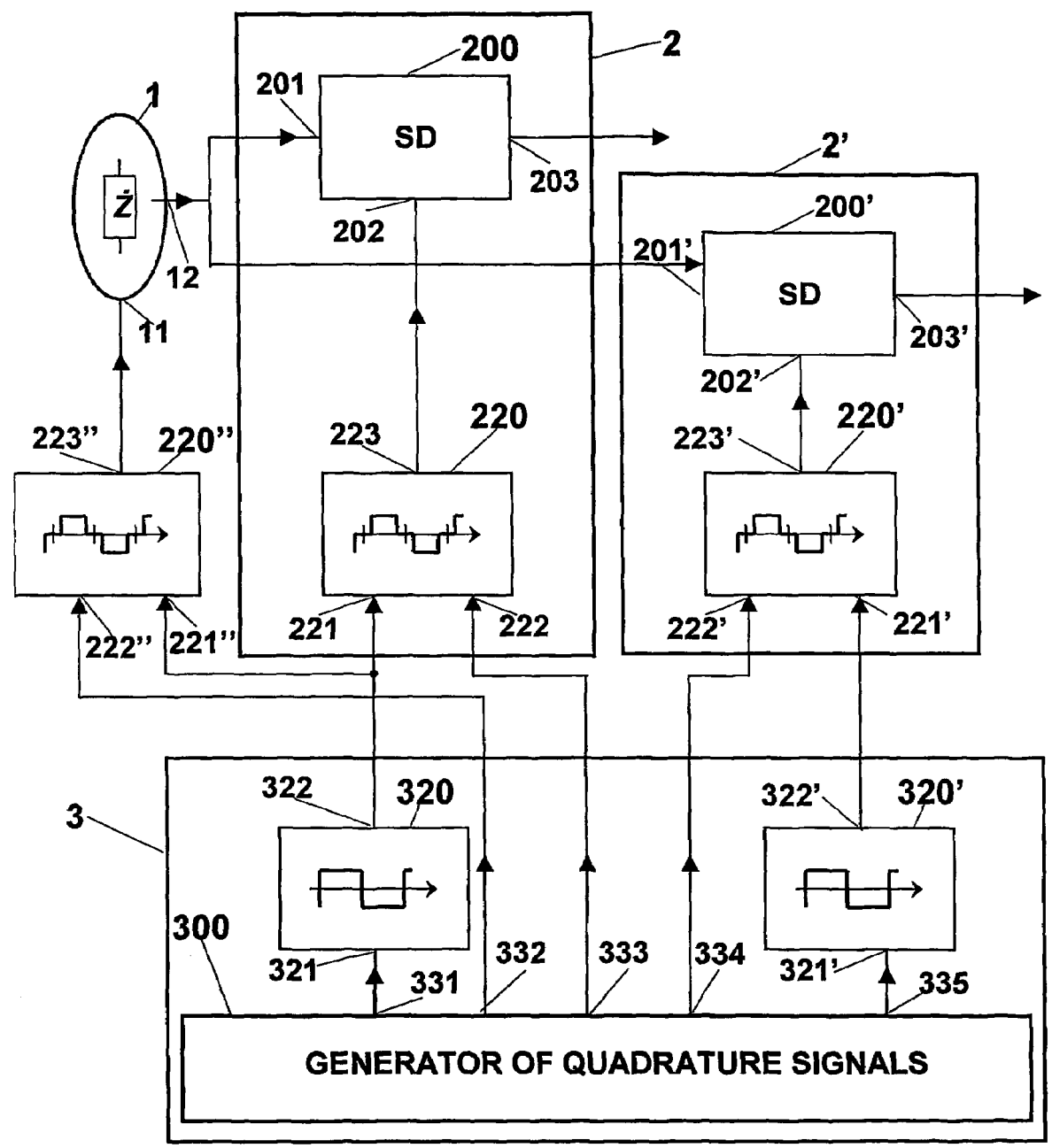
FIG. 3 is a principal block diagram of the two channel measurement device for measuring of mutually quadrature components of the bio-impedance according to the method presented in FIG. 1.

A device for measuring of an electrical bio-impedance in FIG. 3 has two identically designed but functionally differently connected quadrature measurement channels 2 and 2', and a generator of quadrature driving signals 3, which includes of two formers of the bipolar rectangular signal 320 and 320', the corresponding inputs 321 and 321' of which are connected to the quadrature outputs 331 and 335 of the generator of quadrature signals 300, respectively. Output 332 of the former of the bipolar rectangular signal 320 is connected to the input 221 of the device for generating shortened pulse 220, and also with the input 221" of the device for generating shortened pulse 220".

The measurement channel 2 contains of the synchronous detector 200 and the device for generating shortened pulse 220, the output 223 of which is connected to the input 202 of the synchronous detector 200, and the second input 222 of which is connected to the second, auxiliary signal output 333 of the generator of quadrature signals 300. The input 201 of the synchronous detector 200 is connected to the output 12 of the bio-object 1, and the output 203 of the synchronous detector 200 is accordingly also the first output of the device.

The measurement channel 2' includes the synchronous detector 200' and the device for generating shortened pulse 220', the output 223' of which is connected to the input 202' of the synchronous detector 200', and the second input 222' of which is connected to the auxiliary signal output 334 of the generator of quadrature signals 300. Input 201' of the synchronous detector 200' is connected to the output 12 of the bio-object 1, and the output 203' of the synchronous detector 200' is accordingly also the second output of the device.

The second input 222' of the device for generating shortened pulse 220" and applying the excitation signal to the bio-object 1 is connected to the assisting auxiliary signal output 332 of the generator of quadrature signals 300, and the output 223" is connected to the input 11 of the bio-object 1.

Figure 4:
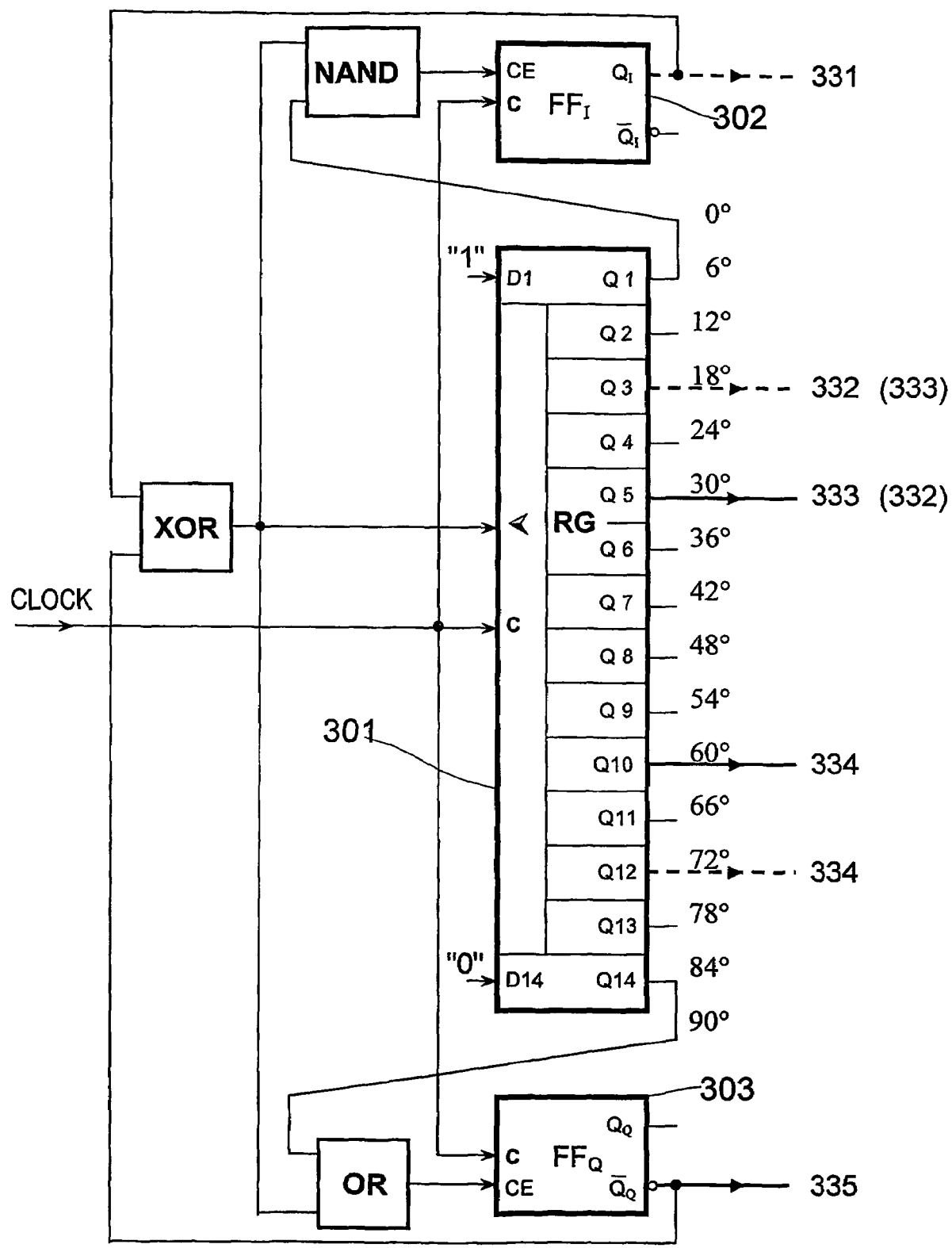
FIG. 4 is a circuitry of a generator of the rectangular wave signals based on using of a shift register and quadrature triggers.
Figure 5:
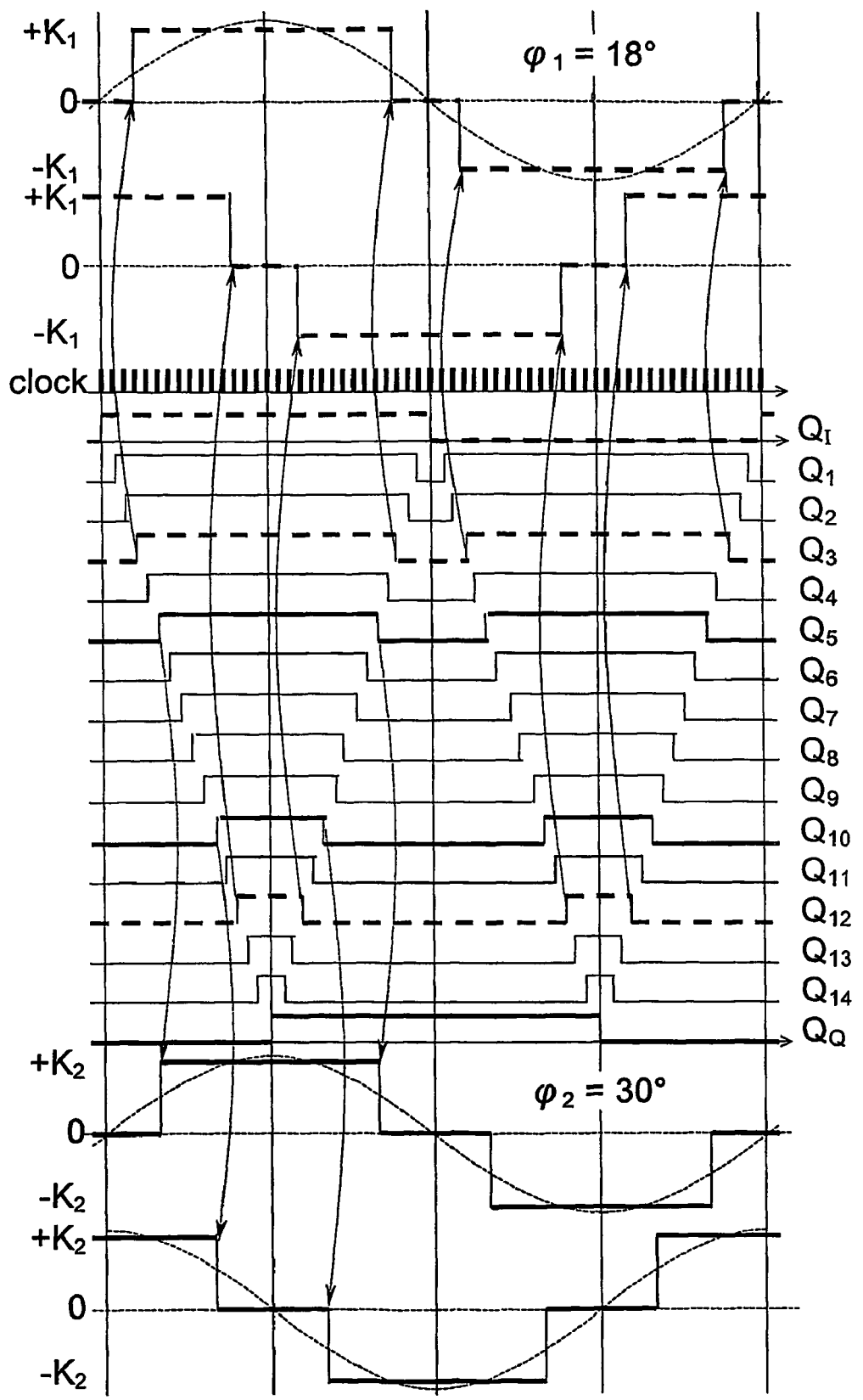
FIG. 5 indicates the rectangular waveforms of signals generated by the generator depicted in FIG. 4, the arrows at the waveforms explain the signal formation procedures.

The generator 300 of quadrature signals (FIG. 4) includes a reversible shift register 301 having a predetermined number of stages, and quadrature triggers 302 and 303, the task of which is to form rectangular, mutually quadrature signals 331 and 335 having the frequency of the fundamental, and the assisting auxiliary signals 333 and 334 for shortening of the rectangular signals 331 and 335, and also assisting auxiliary signal 332 for shortening of the rectangular signal used for excitation of the bio-object 1. In FIG. 5 there are presented time diagrams of the signals explaining the functioning of the generator of driving signals.

Figure 6:
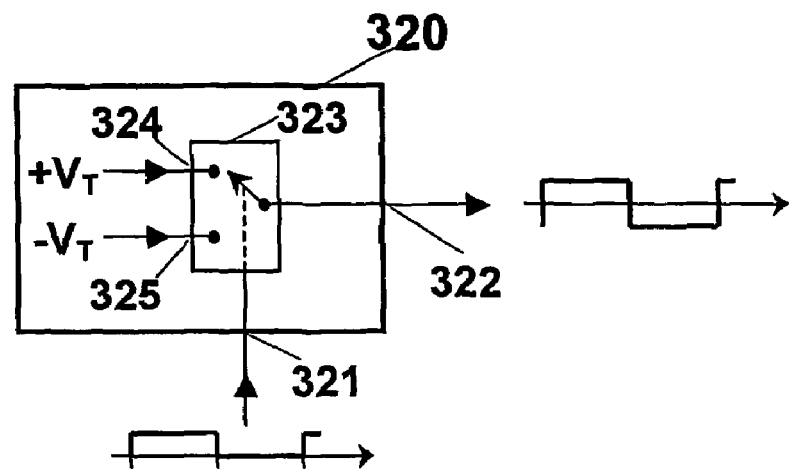
FIG. 6 is a generator of bipolar rectangular signals, whereby the signal waveforms are shown at the inputs and outputs.

Former 320 of the bipolar rectangular signal (FIG. 6) includes a two-pole switch 323, which is controlled by means of the input 321, and the first input 324 of the switch is connected to the positive reference voltage $+V_T$, and the second input 325 of said switch is connected to the negative reference voltage $-V_T$ having equal absolute value, the task of the former 320 is to shape the rectangular form signal received from the generator of quadrature signals 300 into the bipolar rectangular signal.

The device for generating of shortened pulse 220 (FIG. 7) includes a two-pole switch 224 controlled through the input 222, the first input 225 of the switch is connected to the ground, and the second input 226 is connected to the input 221 of said device 220, and the task the device 220 is to shorten the pulses of the bipolar rectangular signal applied to the input of synchronous detector 200 in accordance with the assisting auxiliary signal from the generator of quadrature signals 300.

Figure 8A:
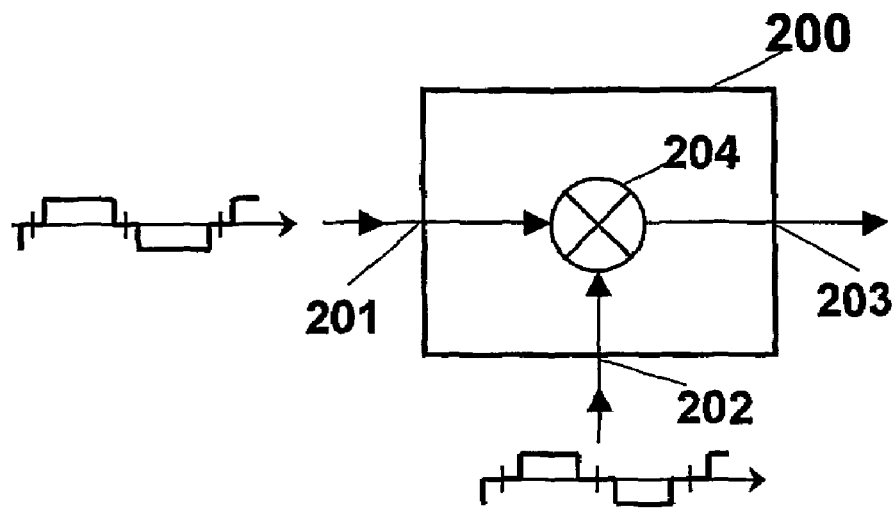
FIG. 8A is a synchronous detector based on an analogue multiplier, whereby the signal waveforms are shown at the inputs.

If need be, the synchronous detector 200 can be designed either on the basis of an analog multiplier 204 (FIG. 8A) or on the basis of switching multiplier (FIG. 8B) including a the three-position switch 250, an amplifier 251 having positive transfer coefficient +K, and the output 253 of the latter is connected to the first input 255 of the switch 250, and an amplifier 252 having a negative transfer coefficient −K, the output 254 of which is connected to the third input 257 of the switch 250. The second input 256 of the switch is, according to the needs, either connected or not connected to the ground, thus providing a zero value transfer factor for the synchronous detector 200 in accordance with the position and duration of the zero value interval in the bipolar rectangular signal applied to the reference input 202.

The measuring device with two measurement channels (FIG. 3) functions as follows: the bio-object is excited with the bipolar rectangular signal having shortened pulse, the corresponding electrical reaction of the bio-object to said signal is measured by means of two identical by their realization but different in their functional connections measurement channels, whereby one of these channels measures the real part R and the second one measures the imaginary part X of the impedance $\dot{Z}=R+jX$ of the bio-object.

Symmetrical rectangular signals of fundamental frequency (FIG. 5) and doubled frequency=auxiliary signals for shortening the pulses of the quadrature rectangular signals and the excitation signal needed for functioning of the device, are generated by the generator of quadrature control signals 300. From the signals obtained from the outputs of the quadrature triggers the formers of the bipolar rectangular signal 320 and 320' (FIG. 5) form the bipolar rectangular signals, into which by the devices for generating of shortened pulse 220, 220' and 220" the zero value intervals, having durations determined according to the auxiliary signals, are introduced, which are needed for eliminating of the $3^{rd}$ and the $5^{th}$ harmonics from the spectra of signals.

Figure 8B:
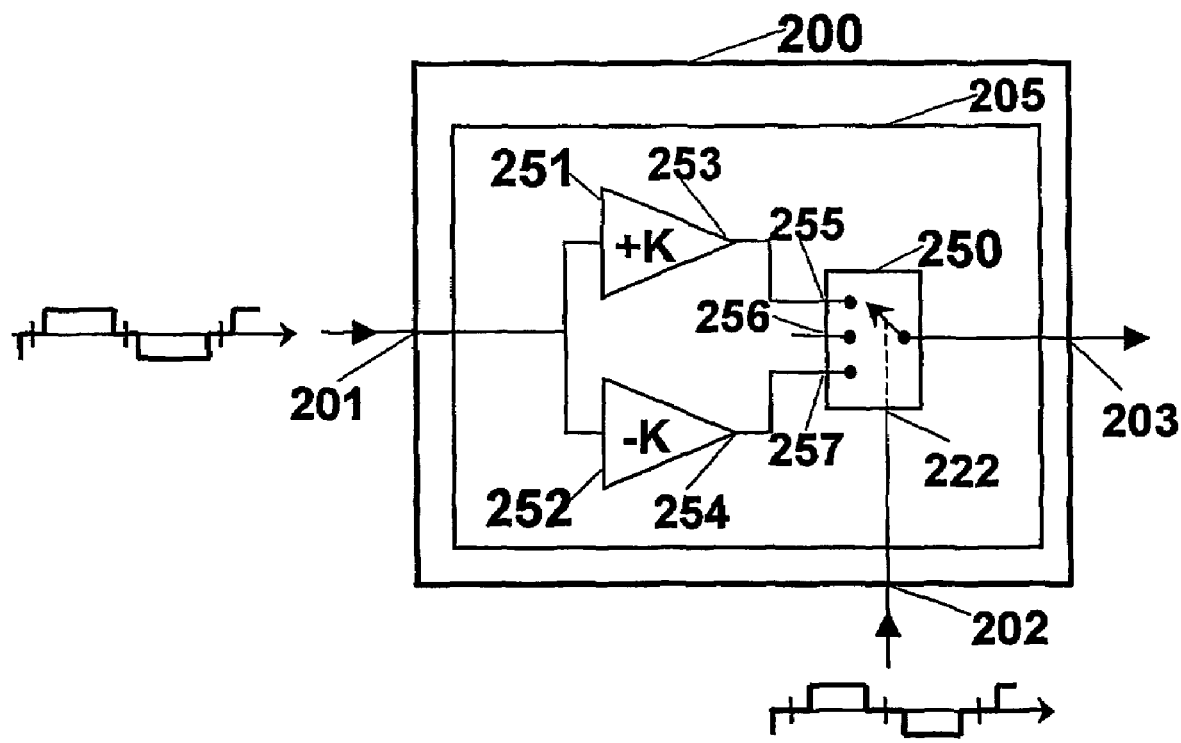
FIG. 8B is a synchronous detector based on using of a switching mode multiplier, whereby the signal waveforms are shown at the inputs.

The measuring channel includes a synchronous detector, which can, according to the needs, be implemented on the basis of an analog multiplier (FIG. 8A), or on the basis of switching mode multiplier (drawing in FIG. 8B). In the both cases a bipolar rectangular signal with shortened pulses is applied to the reference input of the multiplier, with which in case of the analog multiplier the measurable signal is multiplied directly, and which in case of switching mode multiplier is used to control the three-positional switch. The switching mode multiplier can be implemented using both the analogue and/or digital techniques. Commonly the synchronous detector is followed by a circuitry containing a low pass filters and amplifiers, which are not discussed herein in detail, which are used for separating the desired measurand from the output signal of the synchronous detector and amplifying it to a level needed for the equipment which follows the device.

What is claimed is:

1. A device for measuring of an electrical impedance, of an object, comprising:
    an in-phase and a quadrature measurement channels;
    a generator of driving signals;
    a circuit of an excitation signal, the output of which is connected to an input of the object, wherein first and second outputs of the generator of driving signals are connected to inputs and of reference circuits of synchronous detectors, wherein the generator of driving signals comprises a generator of quadrature signals and two formers of the bipolar rectangular signals;
    the circuit of the excitation signal comprises a device for generating a shortened pulse, the control input of which is connected to the output of the auxiliary signal of the generator of quadrature signals, the input is connected to the output of the former of the bipolar rectangular signal, and the output is connected to the input of the bio-object;
    the reference voltage circuit of the synchronous detector of the in-phase measurement channel comprises a device for generating of shortened pulse is introduced, the control input of which is connected to the output of the auxiliary signal of the generator of quadrature signals, the input is connected to the output of the former of the bipolar rectangular signal, and the output is connected to the reference input of the synchronous detector;
    the reference circuit of the synchronous detector of the quadrature measurement channel comprises a device for generating of shortened pulse, the control input of which is connected to the output of the auxiliary signal of the generator of quadrature signals, the input is connected to the output of the former of the bipolar rectangular signal, and the output is connected to the reference input of the synchronous detector.

2. The device according to claim 1, wherein the generator of quadrature signals comprises a shift register of predetermined bit length and the quadrature triggers.

3. The device according to claim 2, wherein the switching multiplier in the synchronous detectors is implemented on the basis of digital techniques.

4. The device according to in claim 1, wherein the synchronous detectors are implemented on the basis of an analog multiplier.

5. The device according to claim 1, wherein the synchronous detectors are implemented on the basis of a switching multiplier.

6. The device according to claim 4, wherein the switching multiplier in the synchronous detectors is implemented on the basis of mixed signal analogue/digital techniques.

* * * * *